United States Patent [19]

Watanabe et al.

[11] Patent Number: 4,729,018
[45] Date of Patent: Mar. 1, 1988

[54] ENDOSCOPE APPARATUS WITH ROTATING SHUTTER

[75] Inventors: Hitoshi Watanabe, Atsugi; Yuuichi Muranaka, Ootawara, both of Japan

[73] Assignee: Kabushiki Kaisha Toshiba, Kawasaki, Japan

[21] Appl. No.: 909,039

[22] Filed: Sep. 19, 1986

[30] Foreign Application Priority Data

Sep. 24, 1985 [JP] Japan .................. 60-208845
Sep. 27, 1985 [JP] Japan .................. 60-212103

[51] Int. Cl.$^4$ .............................................. H04N 7/18
[52] U.S. Cl. ................................ 358/98; 120/6; 362/282
[58] Field of Search ................ 358/98; 128/4, 6; 362/277, 282

[56] References Cited

U.S. PATENT DOCUMENTS

| | | | |
|---|---|---|---|
| 3,166,623 | 1/1965 | Waidelich, Jr. ........... | 358/98 |
| 4,233,650 | 11/1980 | Hagner et al. ........... | 362/322 |
| 4,425,599 | 1/1984 | Rieder et al. ........... | 362/277 |
| 4,475,539 | 10/1984 | Konomura ........... | 358/98 |
| 4,527,552 | 7/1985 | Hattori ........... | 128/6 |
| 4,601,284 | 7/1986 | Arakawa et al. ........... | 128/6 |
| 4,625,236 | 11/1986 | Fujimori et al. ........... | 358/98 |
| 4,631,582 | 12/1986 | Nagasaki et al. ........... | 358/98 |

Primary Examiner—Howard W. Britton
Assistant Examiner—John K. Peng
Attorney, Agent, or Firm—Finnegan, Henderson, Farabow, Garrett & Dunner

[57] ABSTRACT

An endoscope apparatus includes a solid-state image pickup device, a video processor, a light source, a rotating shutter, a light transmission unit, and a display. The solid-state image pickup device for picking up an image of a body cavity is mounted at the distal end of an insertion portion inserted in the body cavity. A signal from the solid-state image pickup device is converted into a video signal by the video processor. An effective transmission interval of light from the light source for emitting continuous illumination light is controlled by a rotating shutter with a shutter blade rotated in synchronism with the video signal. Light transmitted through the rotating shutter is guided to the photographing portion for the solid-state image pickup portion. The video signal from the video processor is displayed at the display.

15 Claims, 13 Drawing Figures

FIG. 3A
FIG. 3B
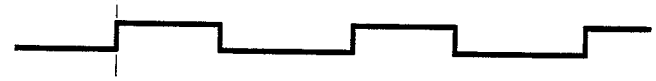
FIG. 3C
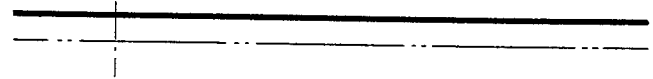
FIG. 3D
FIG. 4
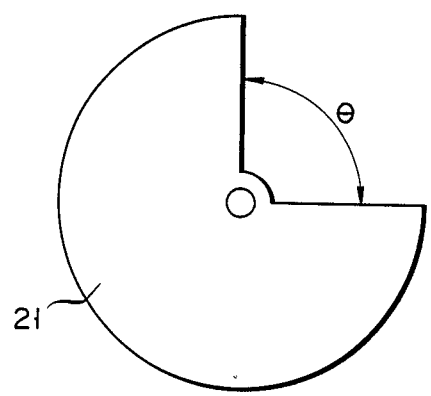

ENDOSCOPE APPARATUS WITH ROTATING SHUTTER

BACKGROUND OF THE INVENTION

The present invention relates to an endoscope apparatus using a solid-state image pickup device which is inserted in a body cavity to pick up an image thereof.

A typical conventional endoscope apparatus uses a fiberscope having an image guide with a bundle of optical fibers.

An improved conventional endoscope has been proposed along with the development of a very compact solid-state image pickup device in recent years. In such an endoscope, the solid-state image pickup device is mounted in the distal end of an insertion portion of the endoscope, and an image of an object to be examined is directly picked up and extracted as a video signal without using an image guide fiber. The extracted video signal is displayed as an image on a TV monitor. Medical diagnosis according to this apparatus is performed through the TV monitor.

In the solid-state image pickup device, signal charges stored in light-receiving portions upon reception of light therein are transferred to vertical transfer portions from the light-receiving portions during the blanking period. When this transfer is completed, new signal charges are started. The transferred charges are sequentially transferred to a horizontal transfer portion according to a TV (scanning) system and then extracted outside the solid-state image pickup device. Illumination of a photographing portion in the body cavity may be performed regardless of the type of light, i.e., continuous light or light pulses.

Diagnosis and therapy using an endoscope are performed such that a doctor observes an image on a real-time basis. An image may be photographed to perform an objective diagnosis and to check an effect of the treatment.

In a conventional endoscope using a fiberscope, a camera is attached to the eyepiece of the probe to take a picture of the object to be examined. In this case, an exposure time can be arbitrarily determined by a shutter speed of the still camera to obtain an image without blurring in a short exposure period. Underexposure is compensated by a flash light source or the like, and thus an exposure time can be further shortened.

In a conventional endoscope apparatus using a solid-state image pickup device, since an image on a TV monitor is photographed, the display image must be frozen (the display image is temporarily processed to obtain a still image). More specifically, a frame memory is arranged in a video processor for processing an image signal. One-frame image data is stored in the frame memory, and the stored image data is repeatedly read out and displayed to obtain a still image. According to a standard interlaced scanning system such as an NTSC (National Television System Committee), a period required for forming a one-field image is 1/60 sec, and a period required for forming a one-frame image is 1/30 sec corresponding to the two-field time. If an image to be stored in the frame memory is a one-frame image, a time lag of about 1/30 sec occurs. Even if a one-field image is written in the frame memory, a time lag of 1/60 sec occurs. In particular, if a dynamic body portion such as an esophagus subjected to an influence of heart beats is to be photographed, blurring typically occurs. Such blurring degrades not only the quality of the still image but also of the moving image.

In order to observe a body cavity with an endoscope, the intensity of illumination light must be controlled according to brightness of an object to be examined, e.g., a body cavity wall. In a conventional endoscope apparatus using an image guide fiber, the brightness of the object is measured through the image guide fiber, and control is provided to set the measured value within a predetermined range.

A portion as an object to be examined with an endoscope is a spatially narrow portion. However, in such a narrow portion, portions to be examined have significantly different distances from the distal end of the insertion portion of the endoscope and have different brightness levels.

SUMMARY OF THE INVENTION

It is an object of the present invention to provide an endoscope apparatus for effectively correcting brightness variations in observation portions caused by different distances from an image pickup portion and for obtaining an image with little blurring for a dynamically moving portion to be examined.

In an endoscope apparatus according to the present invention, light from a light source for generating continuous light is intermittently shielded by a rotary shutter to produce light pulses, the light pulses are emitted onto a portion to be examined, and an intensity of illumination light is controlled according to a radiation time interval measured by the rotary shutter.

According to the endoscope apparatus having a solid-state image pickup device at a distal end of an insertion portion, the brightness variations of the photographing portions caused by different distances from the image pickup portion can be effectively corrected to obtain an image with little blurring for a dynamically moving portion to be examined. In particular, image information is stored in the frame memory, and a still image with little blurring can be obtained when the image is frozen. In addition, the light source itself can generate continuous light so that degradation of the light source such as a lamp can be minimized.

BRIEF DESCRIPTION OF THE DRAWINGS

FIGS. 3A to 3D are timing charts for explaining the operation of the apparatus in FIG. 1;

FIG. 4 is a schematic view showing a shape of a light-shielding portion of a shutter blade used in the apparatus of FIG. 1;

DETAILED DESCRIPTION OF THE PREFERRED EMBODIMENTS

Figure 1:
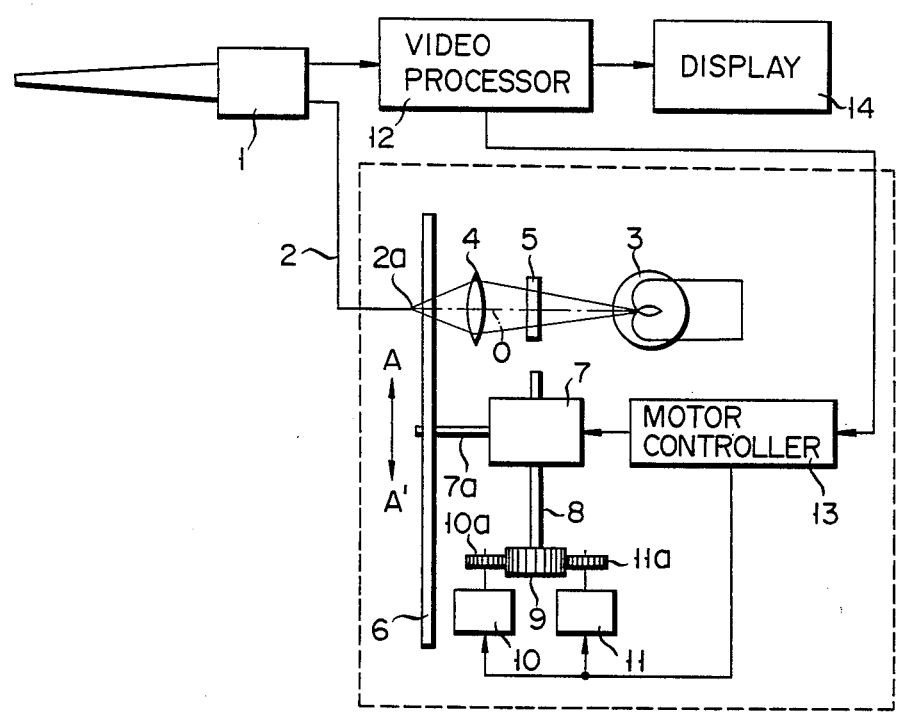
FIG. 1 is a schematic diagram showing an endoscope apparatus according to a first embodiment of the present invention.

FIG. 1 shows the overall system configuration of an endoscope apparatus according to a first embodiment of the present invention.

The endoscope apparatus in FIG. 1 comprises endoscope insertion portion 1, light guide 2, light source 3, condenser lens 4, infrared cut filter 5, shutter blade 6, first motor 7, lead screw 8, first gear 9, second and third motors 10 and 11, video processor 12, motor controller 13, and display 14.

A photographing optical system including an objective lens and a solid-state image pickup device of a CCD (Charge-Coupled Device) is incorporated in the distal end of insertion portion 1. One end, i.e., output end of light guide 2 is located at the distal end insertion portion 1. Illumination light guided through light guide 2 is emitted from the distal end of insertion portion 1. Light guide 2 extends through the interior of insertion portion 1 and appears outside at the proximal end of insertion portion 1. Light source 3 emits, e.g., white light. Source 3 is turned on in synchronism with a power source of the apparatus and emits continuous light. Light from light source 3 is focused by condenser lens 4 onto the other end, i.e., input end 2a of light guide 2. Light emitted from light source 3 and incident on input end 2a of guide 2 is guided through insertion portion 1 by light guide 2 to an object to be examined. Light is emitted from the distal end of insertion portion 1 to the portion to be examined or observed. Infrared cut filter 5 is inserted between light source 3 and condenser lens 4 to eliminate heat wave from the illumination optical path.

Shutter blade 6 comprises a light-shielding plate of a rotary shutter. Blade 6 is rotated by first motor 7 to block the illumination optical path between condenser lens 4 and light guide 2. The shape of blade 6 will be described later.

First motor 7 and shutter blade 6 are driven and moved together along the A—A' direction upon rotation of lead screw 8. If the rotational direction of lead screw 8 is reversed, the movement direction of motor 7 and blade 6 is also reversed. First gear 9 is fixed to one end of lead screw 8. Gear 9 is meshed with second and third gears 10a and 11a respectively driven by second and third motors 10 and 11. One of motors 10 and 11 is used as a forward rotation motor, and the other is used as a reverse rotation motor so as to drive lead screw 8 in opposite directions. For this purpose, oneway clutches (not shown) are respectively arranged between gear 10a and motor 10 and between gear 11a and motor 11. Motors 10 and 11 may be replaced with a single reversible motor. In this case, lead screw 8 is drive directly by the reversible motor or indirectly through a gear.

Video processor 12 receives an electrical signal from the solid-state image pickup device of, e.g., a CCD (Charge-Coupled Device) arranged at the distal end of insertion portion 1 and performs predetermined processing. Processor 12 determines according to a signal from the solid-state image pickup device whether an amount of light emitted onto the photographing portion (detected intensity) is set to an optimal (predetermined intensity) value. Processor 12 supplies to motor controller 13 an intensity control signal corresponding to the light detection data and a frame rate signal of a video signal obtained by the solid-state image pickup device. Motor controller 13 receives the intensity control signal and the frame rate signal and controls motors 7, 10 and 11. More specifically, motor controller 13 synchronizes motor 7 for driving shutter blade 6 with the video frame rate in response to the frame rate signal, i.e., a frame sync signal. Controller 13 controls rotation of motor 10 or 11 for controlling the light intensity in response to the intensity control signal. Video processor 12 responds to the electrical signal from the solid-state image pickup device and outputs a video signal for displaying a continuous image constituting a moving image and a still image stored in the frame memory. Display 14 displays an image represented by the video signal.

The shape of shutter blade 6 will be described below.

Figure 2:
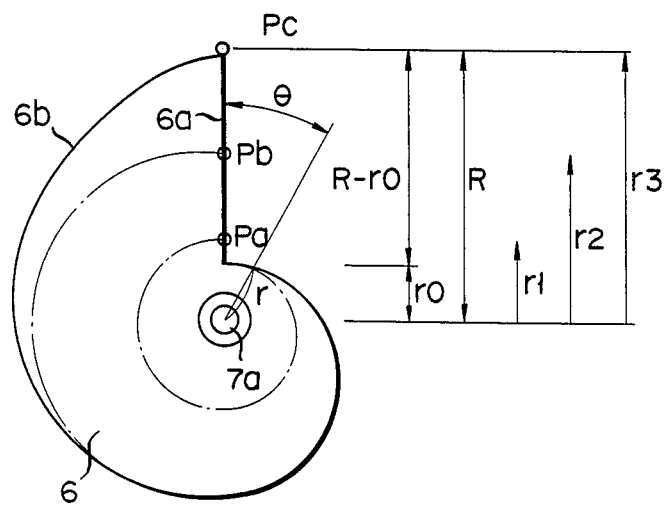
FIG. 2 is a schematic view showing shapes of light-shielding portions of a shutter blade used in the endoscope apparatus of FIG. 1.

As shown in FIG. 2, shutter blade 6 has a shape such that a transmission interval of illumination light from light source 3 changes when the relative positions of optical axis O of the illumination optical path and rotating shaft 7a of blade 6, i.e., a gap therebetween is changed. Referring to FIG. 2, blade 6 has arcuated outer edge 6b such that dimensions passing through points Pa, Pb, and Pc (at different distances from the center) on radial reference edge 6a are different. Angle $\theta$ of counterclockwise rotation of reference edge 6a is given as follows:

$$\theta = (r - r0)/(R - r0) \times 360 \text{ degrees}$$

where
R: the distance from rotating shaft 7a to Pc, i.e., the maximum radius of shutter blade 6
r0: the minimum radius of blade 6
r: the distance from shaft 7a to outer edge 6b of blade 6 when edge 6a is rotated counterclockwise through angle $\theta$ If r=r1, r2, and r3 (where r1, r2, r3 are the distances from rotating shaft 7a to points Pa, Pb, and Pc wherein r3=R), corresponding angles $\theta 1$, $\theta 2$, and $\theta 3$ satisfy the following inequality:

$$0 < \theta 1 < \theta 2 < \theta 3 = 360 \text{ degrees}$$

The light-shielding interval upon rotation of shutter blade 6 under the condition where illumination optical paths are respectively located at points Pa, Pb, and Pc corresponds to angles of the light-shielding portions having radii r1, r2 and r3. Illunination light intervals are obtained upon rotation of blade 6, as shown in FIGS. 3B to 3D. Assume that the illumination optical paths are located at points Pa and Pb. As shown in FIG. 3A, light pulses are synchronized with the frame rate. The pulse width for point Pb is wider than that for point Pa. When the illumination optical path is located at point Pc, continuous light is emitted, as shown in FIG. 3D.

An observation of a body cavity by using the endoscope apparatus having the arrangement described above will be described.

Insertion portion 1 is inserted inside the body cavity, and light source 3 is turned on. Light from light source 3 is emitted from the distal end of insertion portion 1 to a photographing object through light guide 2. Light reflected by the photographing object, i.e., light for forming an image of the photographing object is incident on a solid-state image pickup device incorporated in the distal end of insertion portion 1. An electrical signal from the image pickup device is converted into a video signal in video processor 12 and displayed as an image on display 14.

In this case, shutter blade 6 is rotated at a predetermined angular speed in synchronism with the video frame rate. At the same time, the light intensity control signal is supplied from video processor 12 to motor controller 13, and then motor 10 or 11 is rotated to shift the position of blade 6 with respect to optical axis O. The light-shielding time of illumination light at the position of axis O is controlled. Therefore, the light pulse width is changed to correspond to the intensity control signal supplied to processor 12. For this reason, the intensity of light emitted from light source 3 is kept unchanged. At the same time, while the shutter blade is rotated at a predetermined speed synchronized with the video frame rate, the pulse width of the light pulse emitted onto the photographing object, i.e., the radiation time per frame can be optimally controlled.

If control is performed to obtain an optimal light intensity in the endoscope apparatus, a higher intensity is required for a far photographing object and the radiation time is prolonged. In this case, blurring tends to occur. However, if a distance to the photographing object is long, motion on the screen is small and therefore blurring does not present a critical problem.

Irregular rotation of shutter blade 6 influences precision of the light-shielding timing. If shutter blade 6 is asymmetrical about the rotating shaft, a counterweight is preferably arranged or the materials of blade portions are preferably changed, thereby balancing the rotation thereof. Alternatively, if a light-shielding paint is applied to a transparent disc to form a light-shielding portion and hence a shutter blade, rotational balance can be easily achieved. Instead of the shutter blade whose light-shielding angle range is continuously changed upon changes in radius, as shown in FIG. 2, a shutter blade whose light-shielding range is changed in a stepwise manner according to changes in radius may be used. The numbers of light-shielding and light-transmitting portions per revolution may be two or more, respectively.

If light intensity control requires only two modes, i.e., high and low intensity modes, shutter blade 21 having light-transmitting portion with angle $\theta$, as shown in FIG. 4 can be used. In the low intensity mode, a distance between the rotating shaft of blade 21 and the illumination optical path is set to be less than the radius of blade 21, and the light pulse is emitted onto the photographing object. However, in the high intensity mode, the distance exceeds the radius. Blade 21 is deviated from the illumination optical path, and continuous light is emitted onto the photographing object.

Figure 5:
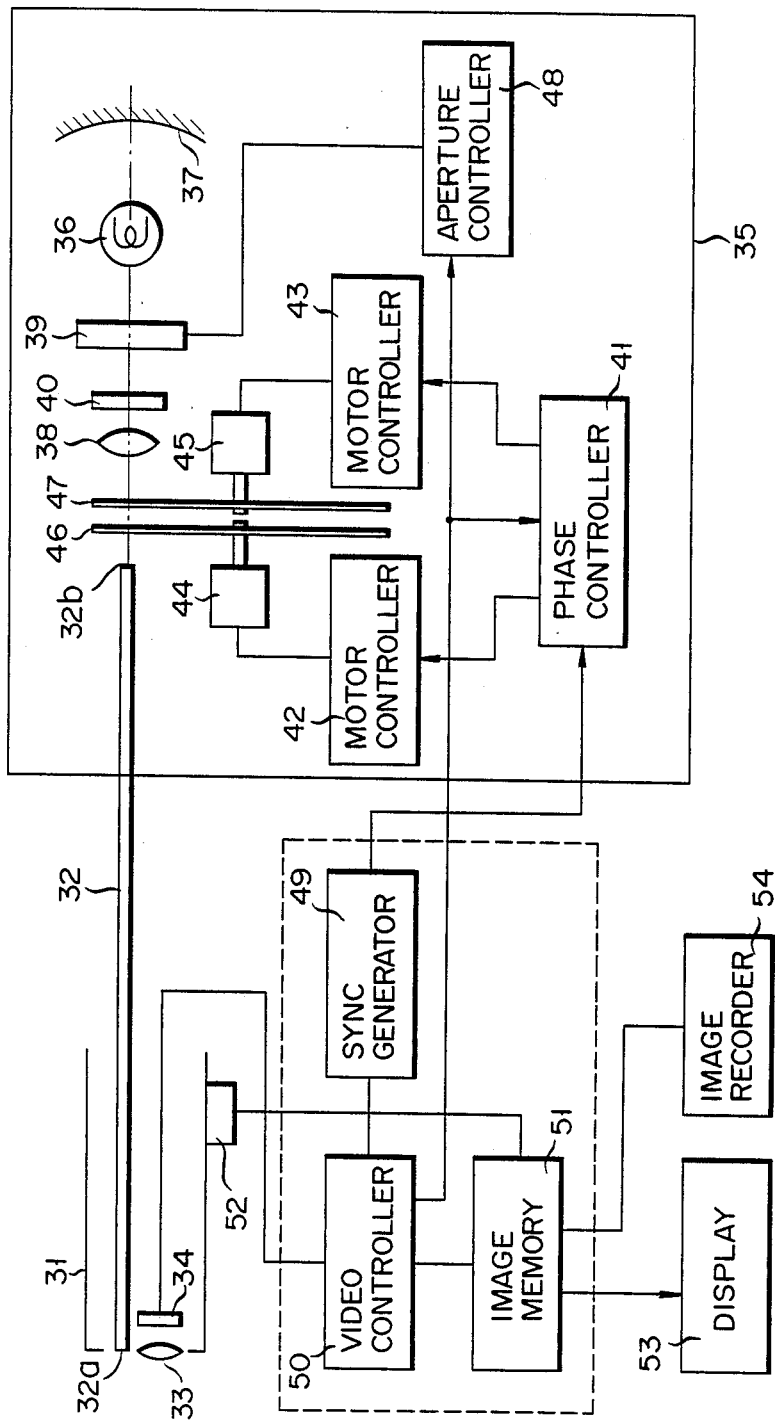
FIG. 5 is a schematic diagram of an endoscope apparatus according to a second embodiment of the present invention.

FIG. 5 shows an arrangement of an endoscope apparatus according to a second embodiment of the present invention.

In the endoscope apparatus of FIG. 5, one end, i.e., light emission portion 32a of flexible light guide 32 for guiding illumination light is disposed at the distal end of endoscope insertion portion 31. Photographing lens 33 and solid-state image pickup device 34 are arranged at the distal end of insertion portion 31. A photographing object is irradiated with illumination light guided through light guide 32 and is picked by device 34 through lens 33. Light source unit 35 supplies illumination light to insertion portion 31 through light guide 32. Light source unit 35 accommodates light source 36, focusing mirror 37, condenser lens 38, variable aperture 39, heat wave absorption filter 40, phase controller 41, first and second motor controllers 42 and 43, first and second motors 44 and 45, first and second shutter blades 46 and 47, and aperture controller 48.

Light source 36 comprises a white light lamp and emits continuous light upon energization of the endoscope apparatus. Mirror 37 is arranged behind light source 36. Light from source 36 is focused by mirror 37 and condenser lens 38 and is incident on the other end, i.e., light input portion 32b of light guide 32. Variable aperture 39 is inserted between light source 36 and condenser lens 38 and is controlled by aperture controller 48 so as to adjust the light intensity. Filter 40 is inserted between variable aperture 39 and condenser lens 38 to absorb infrared rays from light emitted from light source 36. Filter 40 thus transmits only visible light therethrough.

First and second shutter blades 46 and 47 are respectively semicircular shutter blades with an identical radius. Shutter blades 46 and 47 are respectively driven by first and second motors 44 and 45. Motors 44 and 45 are controlled by first and second motor controllers 42 and 43. Controllers 42 and 43 are controlled by phase controller 41 and respectively control first and second motors 44 and 45.

Sync generator 49 controls video controller 50 for converting a signal from image pickup device 34 into a video signal and generates a sync signal for controlling phase controller 41. Image memory 51 is a memory for storing at least a one-frame image. Memory 51 receives and updates the image signals sequentially supplied from video controller 50 and sequentially reads them out. The readout image signal is transferred to display 53 and displayed thereat. When a write instruction is supplied from write instruction switch 52 arranged at part of insertion portion 31 to image memory 51, image memory 51 stops writing and updating the image signal from video controller 50. At the same time, the written image is transferred to image recorder 54. Video controller 50 detects brightness (intensity) of the photographing object and outputs an intensity control signal corresponding to a difference between the detected brightness (intensity) and the optimal (predetermined intensity) value.

Figure 6A:
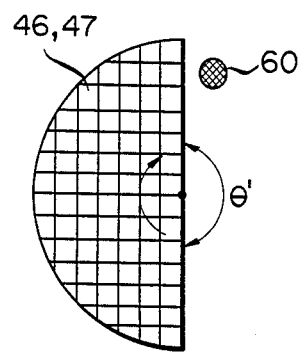
FIGS. 6A and 6B are respectively schematic views showing the constructions of shutter blades used in the apparatus of FIG. 5.
Figure 6B:
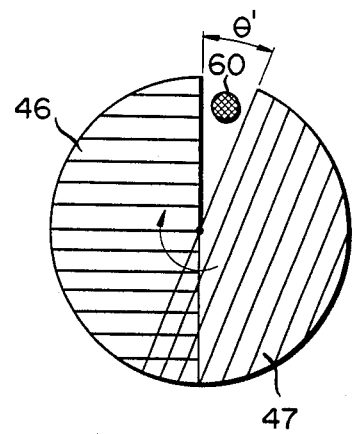
Figure 7A:
FIGS. 7A to 7C are timing charts for explaining the operation of the apparatus in FIG. 5.
Figure 7B:
Figure 7C:

Phase controller 41 receives the sync signal from sync generator 49 and the intensity control signal from controller 50 to rotate motors 44 and 45, hence shutter blades 46 and 47 in synchronism with the frame or field rate in response to the sync signal. Phase controller 41 also provides a phase difference between rotation of blade 46 and rotation of blade 47 according to the intensity control signal. If the phase difference between blades 46 and 47 is zero (i.e., they are completely synchronized with each other), two semicircular shutter blades completely overlap as if only one semicircular shutter is rotated. In this case, angle $\theta'$ of the light-transmitting portion is 180 degrees. If illumination optical path 60 shown in FIG. 6A is shielded, illumination light emitted onto the photographing object is a light pulse having a duty ratio of 50% and synchronized with the frame sync signal (FIG. 7A), as shown in FIG. 7B. By properly changing a phase difference between rotation of blade 46 and rotation of blade 47, angle $\theta'$ of the light-transmitting portion can be varied in the range of 0 to 180 degrees, as shown in FIG. 6B. Therefore, the light pulse corresponding to given angle $\theta'$, as shown in FIG. 7C, is emitted onto the photographing object.

The intensity control signal is also supplied to aperture controller 48. The variable aperture is controlled by controller 48 to adjust the intensity of light guided from light source 36 to condenser lens 38.

When insertion portion 31 of the endoscope apparatus is inserted in the body cavity and light source 36 is turned on, illumination light is emitted from the distal end of insertion portion 31 onto the photographing object through variable aperture 39, heat wave absorption filter 40, condenser lens 38, and light guide 32. An image of light reflected by the photographing object is incident on solid-state image pickup device 34 through photographing lens 34. An output signal from device 34 is converted into a video signal by video controller 50. The video signal is displayed on display 53 through image memory 51.

In this case, shutter blades 46 and 47 are rotated through phase controller 41 and motor controllers 42 and 43 in synchronism with the video signal. Blades 46 and 47 are rotated with a phase difference controlled by phase controller 41. Illumination light is emitted as a light pulse having a pulse width determined by transmission light angle $\theta'$ corresponding to the phase difference.

When a write instruction is generated from write instruction switch 52, write access of image memory 51 is interrupted. A still image is transferred to and displayed at display 53. In this case, the still image is obtained by picking up the image of the photographing object with the light pulse and is thus substantially free from blurring with high quality.

Illumination with light pulses by shutter blades 46 and 47 may be performed during freezing upon operation of switch 52. If an image of the object to be examined is displayed as a moving object, shutter blades 46 and 47 may be removed from the optical path and the photographing object may be irradiated with continuous light. In this case, intensity control is performed by variable aperture 39.

If intensity control can be sufficiently performed (illumination with a light pulse is performed even if a photographing object is displayed as a moving object) by pulse width control using rotational phase control (i.e., control of the transmission light angle), a fixed aperture (aperture controller 48 is omitted) may be used in place of variable aperture 39. Alternatively, variable aperture 39 and aperture controller 48 may be omitted.

The number of light-transmitting portions of the shutter blade need not be one but can be increased to two or more. If the angle of the light-transmitting portion is controlled by a combination of a plurality of shutter blades, the shapes and number of shutter blades may be arbitrarily selected.

The present invention is applicable to an arrangement wherein an image guide is provided in an insertion portion, and the said-state image pickup device provided on the proximal end picks up the image guided through the image guide.

What is claimed is:

1. An endoscope apparatus comprising:
   a solid-state image pickup device, arranged in an insertion portion to be inserted in a body cavity for picking up an image of the body cavity;
   video processing means for performing predetermined processing of a signal from said solid-state image pickup device to produce a video signal;
   a light source for generating a continuous illumination light;
   rotating shutter means including a shutter blade rotated in synchronism with the video signal from said video processing means and shifting means for shifting a relative distance between a rotating axis of said shutter blade and an illumination optical path, said shutter blade having a light-transmitting portion with a predetermined angle range on an edge of said shutter blade and a light-shielding portion with a remaining angle range, the predetermined angle range of said light-transmitting portion being adapted to vary according to different radii, thereby controlling the transmission time of the light from said light source;
   light-transmitting means for guiding light passing through said rotating shutter means to a photographing object for said solid state image pickup device; and
   display means for displaying the video signal obtained by said video processing means.

2. The apparatus according to claim 1, wherein said video processing means includes intensity detecting means for detecting an intensity of an observation object portion in an image and comparing the detected intensity with a predetermined intensity value to produce an intensity control signal, and said rotating shutter means includes means for controlling the light transmission interval in response to the intensity control signal.

3. The apparatus according to claim 1, wherein said video processing means includes an image memory for storing at least one-field image data so as to display a still image.

4. The apparatus according to claim 1, further comprising image recording means for recording the video signal.

5. The apparatus according to claim 1, further comprising a focusing optical system for focusing light from said light source.

6. The apparatus according to claim 1, further comprising filtering means for eliminating infrared rays from light from said light source to obtain predetermined visible light.

7. The apparatus according to claim 1, further comprising variable aperture means for controlling the intensity of light from said light source.

8. An endoscope apparatus comprising:
   a solid-state image pickup device, arranged in an insertion portion to be inserted in a body cavity, for picking up an image of the body cavity;
   video processing means for performing predetermined processing of a signal from said solid-state image pickup device to produce a video signal;
   a light source for generating a continuous illumination light;
   rotating shutter means including a plurality of shutter blades each having a light-transmitting portion with a predetermined angle range on an edge of said shutter blade and a light-shielding portion with a remaining angle range, and angle control means for changing the relative angle formed by said plurality of shutter blades and for controlling the angle range of a total light-emitting portion formed by a combination of said plurality of shutter blades, thereby controlling the transmission time of the light from said light source, said plurality of shutter blades being rotated in synchronism with the video signal from said video processing means;
   light-transmitting means for guiding light passing through said rotating shutter means to a photographing object for said solid state image pickup device; and display means for displaying the video signal obtained by said video processing means.

9. An apparatus according to claim 11, wherein said rotating shutter means includes a plurality of rotating means for synchronously rotating said plurality of shutter blades, and said angle control means changes phase difference of said plurality of rotating means, thereby controlling an angle range of a total light-emitting portion formed by a combination of said plurality of shutter blades.

10. The apparatus according to claim 8, wherein said video processing means includes intensity detecting means for detecting an intensity of an observation object portion in an image and comparing the detected intensity with a predetermined intensity value to produce an intensity control signal, and said rotating shutter means includes means for controlling the light transmission interval in response to the intensity control signal.

11. The apparatus accoring to claim 8, wherein said video processing means includes an image memory for storing at least one-field iamge data so as to display a still image.

12. The apparatus according to claim 8, further comprising image recording means for recording the video signal.

13. The apparatus according to claim 8, further comprising a focusing optical system for focusing light from said ligth source.

14. The apparatus according to claim 8, further comprising filtering means for eliminating infrared rays from light from said light source to obtain predetermined visible light.

15. The apparatus according to claim 8, further comprising variable aperture means for controlling the intensity of light from said light source.

* * * * *